(12) United States Patent
Carpino et al.

(10) Patent No.: US 6,248,717 B1
(45) Date of Patent: Jun. 19, 2001

(54) TARTRATE SALT OF A SUBSTITUTED DIPEPTIDE AS GROWTH HORMONE SECRETAGOGUE

(75) Inventors: Philip Albert Carpino, Groton, CT (US); Paul Andrew Dasilva-Jardine, Providence, RI (US); Bruce Allen Lefker, Gales Ferry; Jerry Anthony Murry, Mystic, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/380,886

(22) PCT Filed: Jun. 5, 1998

(86) PCT No.: PCT/IB98/00874

§ 371 Date: Sep. 7, 1999

§ 102(e) Date: Sep. 7, 1999

(87) PCT Pub. No.: WO98/58948

PCT Pub. Date: Dec. 30, 1998

Related U.S. Application Data

(60) Provisional application No. 60/050,723, filed on Jun. 25, 1997.

(51) Int. Cl.⁷ .................................................. A61K 38/05
(52) U.S. Cl. ............................................. 514/19; 546/119
(58) Field of Search ................................ 514/19; 546/119

(56) References Cited

U.S. PATENT DOCUMENTS

| | | | |
|---|---|---|---|
| 4,411,890 | 10/1983 | Momany | 424/177 |

FOREIGN PATENT DOCUMENTS

| | | | |
|---|---|---|---|
| WO9411012 | 5/1994 | (WO) | A61K/37/00 |
| WO9413696 | 6/1994 | (WO) | C07K/5/02 |
| WO9513069 | 5/1995 | (WO) | A61K/31/445 |
| WO9724369 | 7/1997 | (WO) | C07K/5/06 |

OTHER PUBLICATIONS

The Merck Index, 12$^{th}$ Merck & Co., NJ, 1996 pp. 43, 269, 1487 and 1488.

*Primary Examiner*—F. T. Moezie

(74) *Attorney, Agent, or Firm*—Peter C. Richardson; Gregg C. Benson; Todd M. Crissey

(57) ABSTRACT

This invention is directed to the (L)-tartaric acid salt of 2-amino-N-{1-(2,4-difluoro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo{4,3-c}pyridin-5-yl]-ethyl]-2-methyl-propionamide which is a growth hormone secretagogue and as such is useful for increasing the level of endogenous growth hormone. In another aspect this invention provides certain intermediates which are useful in the synthesis of the foregoing compound. The (L)-tartaric acid salt of the compound of this invention is useful in the treatment and/or prevention of osteoporosis, insulin resistance and other conditions or diseases associated with growth hormone deficiency. The (L)-tartaric acid salt of the compound of the present invention is also useful in treating osteoporosis when used in combination with: a bisphosphonate compound; estrogen, Premarin, and optionally progesterone; an estrogen agonist or antagonist; or calcitonin. Further, the present invention is directed to pharmaceutical compositions. This invention is further directed to methods comprising administering to a human or other animal a combination of an alpha-2 adrenergic agonist and the (L)-tartaric acid salt of the compound of this invention.

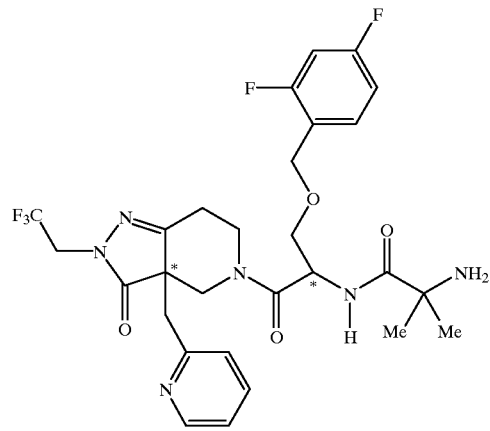

38 Claims, No Drawings

TARTRATE SALT OF A SUBSTITUTED DIPEPTIDE AS GROWTH HORMONE SECRETAGOGUE

This application is the national stage of copending International Patent Application Number PCT/IB98/00874, filed Jun. 5, 1998, which is a continuation of U.S. Provisional Application Ser. No. 60/050,723, filed Jun. 25, 1997.

BACKGROUND OF THE INVENTION

This invention relates to the (L)-(+)-tartaric acid salt of 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide which is a growth hormone secretagogue.

Growth hormone (GH), which is secreted from the pituitary gland, stimulates growth of all tissues of the body that are capable of growing. In addition, growth hormone is known to have the following basic effects on the metabolic processes of the body:

1. Increased rate of protein synthesis in substantially all cells of the body;
2. Decreased rate of carbohydrate utilization in cells of the body; and
3. Increased mobilization of free fatty acids and use of fatty acids for energy.

Deficiency in growth hormone results in a variety of medical disorders. In children, it causes dwarfism. In adults, the consequences of acquired GH deficiency include profound reduction in lean body mass and concomitant increase in total body fat, particularly in the truncal region. Decreased skeletal and cardiac muscle mass and muscle strength lead to a significant reduction in exercise capacity. Bone density is also reduced. Administration of exogenous growth hormone has been shown to reverse many of the metabolic changes. Additional benefits of therapy have included reduction in LDL cholesterol and improved psychological well-being.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in an expensive product, and carried with it the risk that a disease associated with the source of the pituitary gland could be transmitted to the recipient of the growth hormone (e.g., Jacob-Creutzfeld disease). Recently, recombinant growth hormone has become available which, while no longer carrying any risk of disease transmission, is still a very expensive product which must be given by injection or by a nasal spray.

Most GH deficiencies are caused by defects in GH release, not primary defects in pituitary synthesis of GH. Therefore, an alternative strategy for normalizing serum GH levels is by stimulating its release from somatotrophs. Increasing GH secretion can be achieved by stimulating or inhibiting various neurotransmitter systems in the brain and hypothalamus. As a result, the development of synthetic growth hormone-releasing agents to stimulate pituitary GH secretion are being pursued, and may have several advantages over expensive and inconvenient GH replacement therapy. By acting along physiologic regulatory pathways, the most desirable agents would stimulate pulsatile GH secretion, and excessive levels of GH that have been associated with the undesirable side effects of exogenous GH administration would be avoided by virtue of intact negative feedback loops.

Physiologic and pharmacologic stimulators of GH secretion include arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GHRF) or an unknown endogenous growth hormone-releasing hormone or all of these.

This invention also relates to a method of treating insulin resistant conditions such as Non-insulin Dependent Diabetes (NIDD) and reduced glycemic control associated with obesity and aging in a mammal in need thereof which comprises administering to said mammal an effective amount of the L-(+)-tartrate salt of the compound of Formula I, shown below.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low.

WO 94/13696 refers to certain spiropiperidines and homologues which promote release of growth hormone. Preferred compounds are of the general structure shown below.

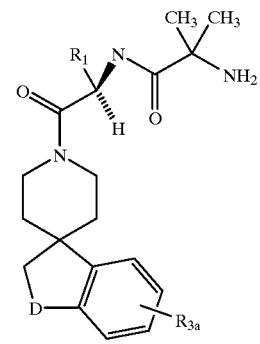

WO 94/11012 refers to certain dipeptides that promote release of growth hormone. These dipeptides have the general structure

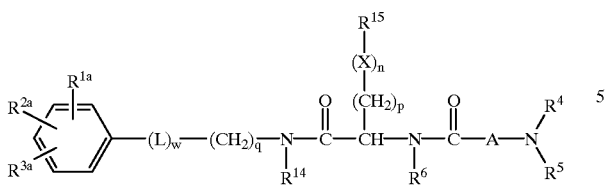

where L is

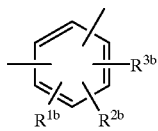

The compounds of WO 94/11012 and WO 94/13696 are reported to be useful in the treatment of osteoporosis in combination with parathyroid hormone or a bisphosphonate.

A generic disclosure of pharmaceutically-acceptable salts of the compound of Formula I of the instant application is disclosed, and the free base of the compound of Formula I of the instant invention is disclosed and claimed, in co-pending PCT Application No. PCT/IB 96/01353 having an international filing date of Dec. 4, 1996, assigned to the assignee hereof.

It has been found that the L-(+)-tartaric acid salt of the compound of Formula I, shown below, can be isolated in crystalline form which has advantageous properties such as ease of making a formulation, high solubility, good stability and is more easily purified than a non-crystalline form.

SUMMARY OF THE INVENTION

This invention provides the L-(+)-tartaric acid salt of the compound of Formula I

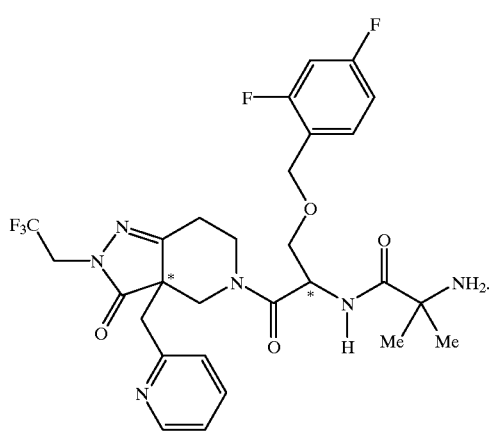

(I)

The "*" indicates a stereochemical center. Preferred of the compound of formula I are the stereochemical mixture or separated isomers having the configurations 3a-(S),1-(R); 3a-(S), 1-(S); 3a-(R), 1-(S); and/or 3a-(R), 1-(R) isomers.

This invention also provides:

a process for the preparation of the (D)-tartaric acid or the (L)-tartaric acid salt of the compound of formula (E),

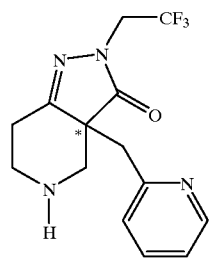

(E)

which comprises reacting the compound of formula (D),

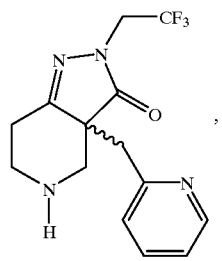

(D)

with (D)-tartaric acid or (L)-tartaric acid in about 8:1 to about 9:1 mixture of acetone:water at a temperature between about 0° C. to room temperature. Preferred of the foregoing process is where (D)-tartaric acid is reacted with the compound of formula (D) and the compound of formula (E) has the R-configuration;

a process for the preparation of the compound of formula (J),

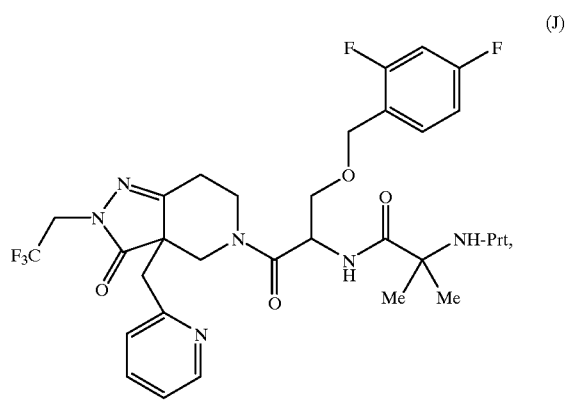

(J)

which comprises reacting the compound of formula (E),

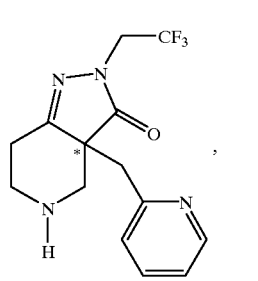

the compound of formula (X),

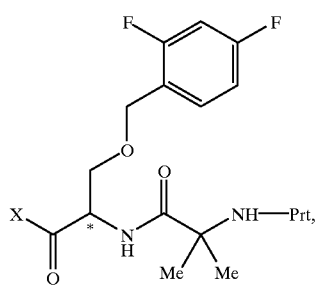

where Prt is an amine protecting group and X is OH, —O(C$_1$–C$_4$)alkyl or halo, the presence of an organic base and a peptide coupling reagent at a temperature between about −78° C. to about −20° C. Preferred of the immediately foregoing process is where the peptide coupling reagent is 1-propane phosphonic acid cyclic anhydride and the compound of formula X has the R-configuration and the compound of formula E has the R-configuration. Even more preferred is a where Prt is tert-butoxycarbonyl in the immediately foregoing process; and a process for the preparation of the (L)-(+)-tartaric acid salt of the compound of formula I,

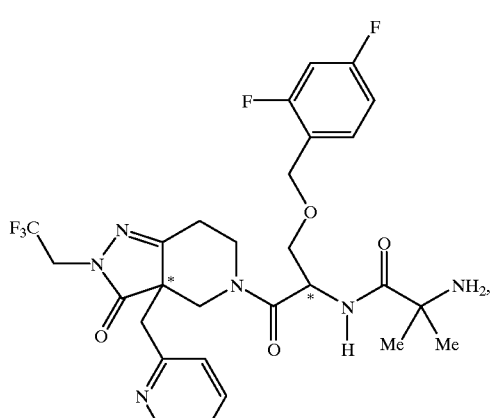

which comprises reacting the compound of formula (E),

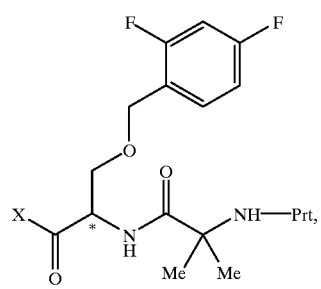

with the compound of formula (X),

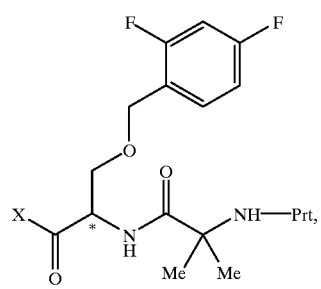

where Prt is an amine protecting group and X is OH, —O(C$_1$–C$_4$)alkyl or halo, in the presence of an organic base and a peptide coupling reagent at a temperature between about −78° C. to about −20° C., to yield the compound of formula (J),

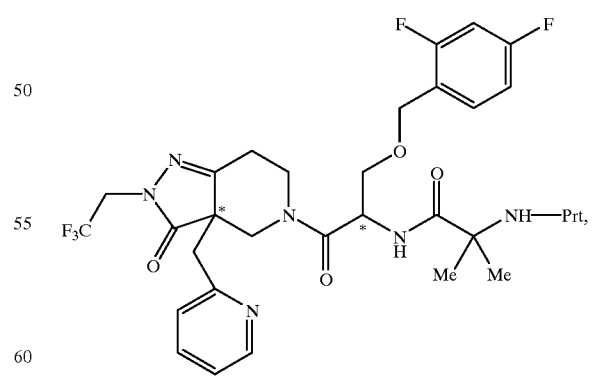

deprotecting the compound of formula (J) under appropriate deprotecting conditions to yield the compound of formula (K),

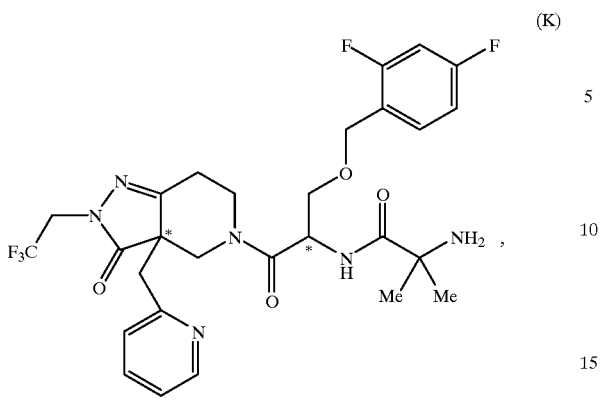

(K)

reacting the compound of formula (K) with (L)-(+)-tartaric acid in a reaction inert solvent to yield the (L)-(+)-tartaric acid salt of the compound of formula I. Preferred of the immediately foregoing process is where Prt is tert-butoxycarbonyl, even more preferred of the immediately foregoing process is where the peptide coupling reagent is 1-propane phosphonic acid cyclic anhydride and the compound of formula I has the absolute and relative configuration 3a-(R), 1-(R).

In another aspect, this invention provides for:
the R,S-enantiomeric mixture, the R-enantiomer or the S-enantiomer of the compound of the formula

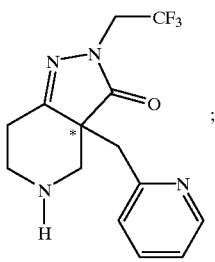

where the (D)-tartaric acid or the (L)-tartaric acid salt is preferred;

the 3a-(R,S),1-(R) diastereomeric mixture, the 3a-(R),1-(R) diastereomer or the 3a-(S),1-(R) diastereomer of the compound of the formula

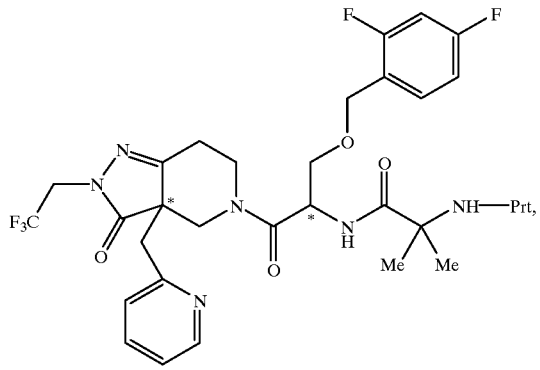

where Prt is an amine protecting group selected from the group consisting of t-BOC, FMOC and CBZ; and
the R,S-enantiomeric mixture, the R-enantiomer or the S-enantiomer of the compound of the formula

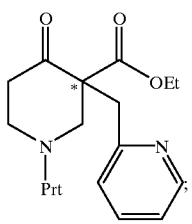

the R,S-enantiomeric mixture, the R-enantiomer or the S-enantiomer of the compound of the formula

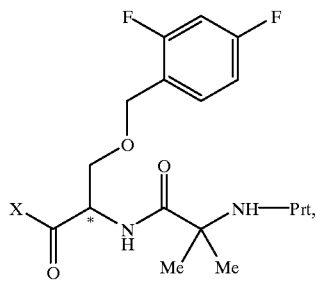

where X is OH, —O($C_1$–$C_4$)alkyl or halo and Prt is an amine protecting group; and where X is OH, Prt is BOC and the stereocenter is in the R-configuration is preferred.

In yet another aspect, this invention provides (where the compound of formula (I) is shown above):

methods for increasing levels of endogenous growth hormone in a human or other animal which comprise administering to such human or animal an effective amount of the (L)-(+)-tartaric acid salt of the compound of formula I;

pharmaceutical compositions which comprise a pharmaceutically-acceptable carrier and an amount of the (L)-(+)-tartaric acid salt of the compound of formula I;

pharmaceutical compositions useful for increasing the endogenous production or release of growth hormone in a human or other animal which comprise a pharmaceutically acceptable carrier, an effective amount of the (L)-(+)-tartaric acid salt of the compound of formula I according to claim 1 and a growth hormone secretagogue selected from the group consisting of GHRP-6, Hexarelin, GHRP-1, growth hormone releasing factor (GRF), IGF-1, IGF-2 and B-HT920 or an analog thereof;

methods for treating or preventing osteoporosis which comprise administering to a human or other animal in need of such treatment or prevention an amount of the (L)-(+)-tartaric acid salt of the compound of formula I which is effective in treating or preventing osteoporosis;

methods for treating or preventing diseases or conditions which may be treated or prevented by growth hormone which comprise administering to a human or other animal in need of such treatment or prevention an amount of the (L)-(+)-tartaric acid salt of the compound of formula I which is effective in promoting release of endogenous growth hormone; preferred is a method wherein the disease or condition is congestive heart failure, obesity or frailty associated with aging; also preferred is a method wherein the disease or condition is congestive heart failure; further preferred is a method wherein the disease or condition is frailty associated with aging;

methods for accelerating bone fracture repair, attenuating protein catabolic response after a major operation, reducing cachexia and protein loss due to chronic illness, accelerating wound healing, or accelerating the recovery of burn patients or patients having undergone major surgery, which methods comprise administering to a mammal in need of such treatment an amount of the (L)-(+)-tartaric acid salt of the compound of formula I which is effective in promoting release of endogenous growth hormone; preferred is a method wherein the method is for accelerating the recovery of patients having undergone major surgery; also preferred is a method wherein the method is for accelerating bone fracture repair;

methods for improving muscle strength, mobility, maintenance of skin thickness, metabolic homeostasis or renal homeostasis, which method comprise administering to a human or other animal in need of such treatment an amount of the (L)-(+)-tartaric acid salt of the compound of formula I which is effective in promoting release of endogenous growth hormone;

methods for the treatment or prevention of osteoporosis which comprise administering to a human or other animal with osteoporosis effective amounts of a bisphosphonate compound and the (L)-(+)-tartaric acid salt of the compound of formula I; preferred of a method for the treatment of osteoporosis is where the bisphosphonate compound is ibandronate; preferred of the method for the treatment of osteoporosis is where the bisphosphonate compound is alendronate;

methods for the treatment or prevention of osteoporosis which comprise administering to a human or other animal with osteoporosis effective amounts of estrogen or Premarin® and the (L)-(+)-tartaric acid salt of the compound of formula I and, optionally, progesterone.

methods for the treatment of osteoporosis which comprise administering to a human or other animal with osteoporosis effective amounts of calcitonin and the (L)-(+)-tartaric acid salt of the compound of formula I;

methods to increase IGF-1 levels in a human or other animal deficient in IGF-1 which comprise administering to a human or other animal with IGF-1 deficiency an effective amount of the (L)-(+)-tartaric acid salt of the compound of formula I;

methods for the treatment of osteoporosis which comprise administering to a human or other animal with osteoporosis effective amounts of an estrogen agonist or antagonist and the of the (L)-(+)-tartaric acid salt of the compound of formula I; preferred is a method wherein the estrogen agonist or antagonist is tamoxifen, droloxifene, raloxifene or idoxifene; also preferred is a method where the estrogen agonist or antagonist is cis-6-(4fluoro-phenyl)-5-[4(2-piperidin-1-yl-ethoxy)-phenyl]-5,6,7,8-tetrahydro-naphthalene-2-ol; (−)-cis-6-phenyl-5-[4-(2-pyrrolidin-1-yl-ethoxy)-phenyl]-5,6,7,8-tetrahydro-naphthalene-2-ol; cis-6-phenyl-5-[-(2-pyrrolidin-1-yl-ethoxy)-phenyl]-5,6,7,8tetrahydro-naphthalene-2-ol; cis-1-[6'-pyrrolodinoethoxy-3'-pyridyl]-2-phenyl-6-hydroxy-1,2,3,4-tetrahydro-naphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-[4-(2-piperidin-1-yl-ethoxy)-phenyl]-5,6,7,8-tetrahydro-naphthalene-2-ol; or 1-(4'-pyrrolidinolethoxyphenyl)-2-phenyl-6-hydroxy- 1,2,3,4-tetrahydro-isoquinoline;

methods for increasing muscle mass, which methods comprise administering to a human or other animal in need of such treatment an effective amount of the (L)-(+)-tartaric acid salt of the compound of formula I;

methods for promoting growth in growth hormone deficient children which comprise administering to a growth hormone deficient child an effective amount of the (L)-(+)-tartaric acid salt of the compound of formula I;

methods for treating insulin resistance in a mammal, which comprise administering to said mammal an effective amount of the (L)-(+)-tartaric acid salt of the compound of formula I; preferred is a method where the condition associated with insulin resistance is type I diabetes, type II diabetes, hyperglycemia, impaired glucose tolerance or an insulin resistant syndrome; also preferred is a method where the condition associated with insulin resistance is associated with obesity or old age;

methods for increasing levels of endogenous growth hormone, which comprise administering to a human or other animal in need thereof effective amounts of a functional somatostatin antagonist and the (L)-(+)-tartaric acid salt of the compound of formula I; preferred is a method where the functional somatostatin antagonist is an alpha-2 adrenergic agonist; and methods of treating or preventing congestive heart failure, obesity or frailty associated with aging, which comprise administering to a human or other animal in need thereof effective amounts of a functional somatostatin antagonist and the of the (L)-(+)-tartaric acid salt of the compound of formula I.

The instant compound of formula I promotes the release of growth hormone, is stable under various physiological conditions and may be administered parenterally, nasally or by the oral route.

DETAILED DESCRIPTION OF THE INVENTION

The (L)-(+)-tartrate salt of the compound of Formula I can be made by the following processes which includes processes known in the chemical arts for the production of compounds. Certain processes for the manufacture of the L-(+)-tartaric acid salt of the compound of Formula I are provided as further features of the invention and are illustrated by the reaction scheme, shown below.

The compound of the instant invention has the absolute and relative configuration shown below:

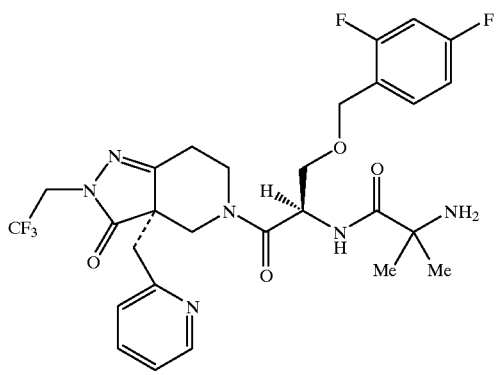

which is designated as the 3a-(R),1-(R) configuration. It can be prepared by the method described hereinbelow.

The growth hormone releasing (L)-(+)-tartaric acid salt of the compound of Formula I is useful in vitro as a unique tool for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the (L)-(+)-tartaric acid salt of the compound of Formula I can be used in the evaluation of how other hormones modify growth hormone releasing activity. For example, it has already been established that somatostatin inhibits growth hormone release.

The (L)-(+)-tartaric acid salt of the compound of Formula I can be administered to animals, including humans, to release growth hormone in vivo. The (L)-(+)-tartaric acid salt of the compound of Formula I is useful for treatment of symptoms related to GH deficiency; to stimulate growth or enhance feed efficiency of animals raised for meat production to improve carcass quality; to increase milk production in dairy cattle; for improvement of bone or wound healing and for improvement in vital organ function, The (L)-(+)-tartaric acid salt of the compound of Formula I by inducing endogenous GH secretion, will alter body composition and modify other GH-dependent metabolic, immunologic or developmental processes. For example, the compounds of the present invention can be given to chickens, turkeys, livestock animals (such as sheep, pigs, horses, cattle, etc.), companion animals (e.g., dogs) or may have utility in aquaculture to accelerate growth and improve the protein/fat ratio in fish. In addition, the (L)-(+)-tartaric acid salt of the compound of Formula I can be administered to humans in vivo as a diagnostic tool to directly determine whether the pituitary is capable of releasing growth hormone. For example, the (L)-(+)-tartaric acid salt of the compound of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, the (L)-(+)-tartaric acid salt of the compound of Formula I in association with a pharmaceutically acceptable carrier. Optionally, the pharmaceutical compositions can further comprise an anabolic agent in addition to the (L)-(+)-tartaric acid salt of the compound of Formula I or another compound which exhibits a different activity, e.g., an antibiotic growth permittant or an agent to treat osteoporosis or with other pharmaceutically active materials wherein the combination enhances efficacy and minimizes side effects.

Growth promoting and anabolic agents are well known in the art and include, but are not limited to, TRH, PTH, diethylstilbesterol, estrogens, β-agonists, theophylline, anabolic steroids, enkephalins, E series prostaglandins, compounds disclosed in U.S. Pat. No. 3,239,345, the disclosure of which is hereby incorporated by reference, e.g., zeranol, compounds disclosed in U.S. Pat. No. 4,036,979, the disclosure of which is hereby incorporated by reference, e.g., sulbenox, and peptides disclosed in U.S. Pat. No. 4,411,890, the disclosure of which is hereby incorporated by reference.

The (L)-(+)-tartaric acid salt of the compound of Formula I in combination with other growth hormone secretagogues such as the growth hormone releasing peptides GHRP-6 and GHRP-1 as described in U.S. Pat. No. 4,411,890, the disclosure of which is hereby incorporated by reference, and publications WO 89/07110, WO 89107111 and B-HT920 as well as hexarelin and the newly discovered GHRP-2 as described in WO 93104081 or growth hormone releasing hormone (GHRH, also designated GRF) and its analogs or growth hormone and its analogs or somatomedins including IGF-1 and IGF-2 or adrenergic agonists such as clonidine, xylazine, detomidine and medetomidine (clonidine, which is disclosed in U.S. Pat. No. 3,202,660 the disclosure of which is hereby incorporated by reference, xylazine, which is disclosed in U.S. Pat. No. 3,235,550 the disclosure of which is hereby incorporated by reference and medetomidine, which is disclosed in US Patent No. 4,544,664 the disclosure of which is hereby incorporated by reference) or serotonin 5HTID agonists such as sumitriptan or agents which inhibit somatostatin or its release such as physostigmine and pyridostigmine, are useful for increasing the endogenous levels of GH in mammals. The combination of the (L)-(+)-tartaric acid salt of the compound of Formula I with GRF results in synergistic increases of endogenous growth hormone.

As is well known to those skilled in the art, the known and potential uses of growth hormone are vaned and multitudinous [See "Human Growth Hormone", Strobel and Thomas, Pharmacological Reviews, 46, pg. 1–34 (1994); T. Rosen et al., Horm Res, 1995; 43: pp. 93–99; M. Degerbiad et al., European Journal of Endocrinology, 1995, 133: pp.180–188; J. O. Jorgensen, European Journal of Endocrinology, 1994, 130: pp. 224–228; K. C. Copeland et al., Journal of Clinical Endocrinology and Metabolism, Vol. 78 No. 5, pp. 1040–1047; J. A. Aloi et al., Journal of Clinical Endocrinology and Metabolism, Vol. 79 No. 4, pp. 943–949; F. Cordido et al., Metab. Clin. Exp., (1995), 44(6), pp. 745–748; K. M. Fairhall et al., J. Endocrinol., (1995), 145(3), pp. 417–426; R M. Frieboes et al., Neuroendocrinology, (1995), 61(5), pp. 584–589; and M. Llovera et al., Int. J. Cancer, (1995), 61(1), pp. 138–141]. Thus, the administration of the (L)-(+)-tartaric acid salt of the compound of Formula I for purposes of stimulating the release of endogenous growth hormone can have the same effects or uses as growth hormone itself. These varied uses of growth hormone may be summarized as follows: stimulating growth hormone release in elderly humans; treating growth hormone deficient adults; preventing catabolic side effects of glucocorticoids; treating osteoporosis; stimulating the immune system; accelerating wound healing; accelerating bone fracture repair; treating growth retardation; treating congestive heart failure as disclosed in PCT publications WO 95128173 and WO 95128174 (an example of a method for assaying growth hormone secretagogues for efficacy in treating congestive heart failure is disclosed in R. Yang et al., Circulation, Vol. 92, No. 2, p.262, 1995); treating acute or chronic renal failure or insufficiency; treating physiological short stature, including growth hormone deficient children; treating short stature associated with chronic illness; treating obesity; treating growth retardation associated with Prader-Willi syndrome and Turner's syndrome; accelerating the recovery and reducing hospitalization of burn patients or following major surgery such as gastrointestinal surgery; treating intrauterine growth retardation, skeletal dysplasia, hypercortisonism and Cushings syndrome; replacing growth hormone in stressed patients; treating osteochondrodysplasias, Noonans syndrome, sleep disorders, Alzheimer's disease, delayed wound healing, and psychosocial deprivation; treating of pulmonary dysfunction and ventilator dependency; attenuating protein catabolic response after a major operation; treating malabsorption syndromes; reducing cachexia and protein loss due to chronic illness such as cancer or AIDS; accelerating weight gain and protein accretion in patients on TPN (total parenteral nutrition); treating hyperinsulinemia including nesidioblastosis; adjuvant treatment for ovulation induction and to prevent and treat gastric and duodenal ulcers; stimulating thymic development and preventing age-related decline of thymic function; adjunctive therapy for patients on chronic hemodialysis; treating immunosuppressed patients and enhancing antibody response following vaccination; improving muscle strength, increasing muscle mass, mobility, maintenance of skin thickness, metabolic homeostasis, renal homeostasis in the frail elderly; stimulating osteoblasts, bone remodeling, and cartilage growth; treating neurological diseases such as peripheral and drug induced neuropathy, Guillian-Barre Syndrome, amyotrophic lateral sclerosis, multiple sclerosis, cerebrovascular accidents and demyelinating diseases; stimulating the immune system in companion animals and treating disorders of aging in companion animals; growth promotant in livestock; and stimulating wool growth in sheep.

It will be known to those skilled in the art that there are numerous compounds now being used in an effort to treat the diseases or therapeutic indications enumerated above. Combinations of these therapeutic agents, some of which have also been mentioned above, with the growth promotant, exhibit anabolic and desirable properties of these various therapeutic agents. In these combinations, the therapeutic agents and the (L)-(+)-tartaric acid salt of the compound of Formula I may be independently and sequentially administered or co-administered in dose ranges from one one-hundredth to one times the dose levels which are effective when these compounds and secretagogues are used singly. Combined therapy to inhibit bone resorption, prevent osteoporosis, reduce skeletal fracture, enhance the healing of bone fractures, stimulate bone formation and increase bone mineral density can be effectuated by combinations of bisphosphonates and the (L)-(+)-tartaric acid salt of the compound of Formula I. See PCT publication WO 95/11029 for a discussion of combination therapy using bisphosphonates and GH secretagogues. The use of bisphosphonates for these utilities has been reviewed, for example, by Hamdy, N. A. T., Role of Bisphosphonates in Metabolic Bone Diseases, Trends in Endocrinol. Metab., 1993, 4, pages 19–25. Bisphosphonates with these utilities include but are not limited to alendronate, tiludronate, dimethyl-APD, risedronate, etidronate, YM-175, clodronate, pamidronate, and BM-210995 (ibandronate). According to their potency, oral daily dosage levels of the bisphosphonate of between 0.1 mg and 5 g and daily dosage levels of the (L)-(+)-tartaric acid salt of the compound of Formula I of between 0.01 mg/kg to 20 mg/kg of body weight are administered to patients to obtain effective treatment of osteoporosis.

The (L)-(+)-tartaric acid salt of the compound of Formula I may be combined with a mammalian estrogen agonist/antagonist. Any estrogen agonist/antagonist may be used as the second compound of this aspect of this invention. The term estrogen agonist/antagonist refers to compounds which bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art according to standard assays including estrogen receptor binding assays, standard bone histomorphometric and densitometer methods (see Eriksen E. F. et al., Bone Histomorphometry, Raven Press, New York, 1994, pages 1–74; Grier S. J. et. al., The Use of Dual-Energy X-Ray Absorptionmetry In Animals, Inv. Radiol., 1996, 31(1):50–62; Wahner H. W. and Fogelman I., The Evaluation of Osteoporosis. Dual Energy X-Ray Absorptionmetry in Clinical Practice., Martin Dunitz Ltd., London 1994, pages 1–296). A variety of these compounds are described and referenced below, however, other estrogen agonists/antagonists will be known to those skilled in the art. A preferred estrogen agonist/antagonist is droloxifene: (phenol, 3-[1-[4[2-(dimethylamino)ethoxy]-phenyl]-2-phenyl 1-butenyl]-, (E)-) and associated compounds which are disclosed in U.S. Pat. No. 5,047,43, the disclosure of which is hereby incorporated by reference.

Another preferred estrogen agonist/antagonist is tamoxifen: (ethanamine,2-[-4-(1,2-diphenyl-1-butenyl)phenoxy]-N,N-dimethyl, (Z)-2-, 2-hydroxy-1,2,3-propanetr-carboxylate (1:1)) and associated compounds which are disclosed in U.S. Pat. No. 4,536,516, the disclosure of which is hereby incorporated by reference. Another related compound is 4-hydroxy tamoxifen which is disclosed in U.S. Pat. No. 4,623,660, the disclosure of which is hereby incorporated by reference.

Another preferred estrogen agonist/antagonist is raloxifene: (methanone, [6-hydroxy-2-(4-hydroxyphenyl)benzo[b]thien-3-yl][4-[2-(1-piperidinyl)ethoxylphenyl]-, hydrochloride) and associated compounds which are disclosed in U.S. Pat. No. 4,418,068, the disclosure of which is hereby incorporated by reference.

Another preferred estrogen agonist/antagonist is idoxifene: pyrrolidine, 1-[-[4-[[1-(4-iodophenyl)-2-phenyl-1-butenyl]phenoxy]ethyl] and associated compounds which are disclosed in U.S. Pat. No. 4,839,155, the disclosure of which is hereby incorporated by reference.

Other preferred estrogen agonist/antagonists include compounds as described in commonly assigned U.S. Pat. No. 5,552,412, the disclosure of which is hereby incorporated by reference. Especially preferred compounds which are described therein are:

cis-6-(4-fluorophenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6 ,7,8-tetrahydro-phthalene-2-ol;

cis-6-phenyl-5-[4-(2-pyrrolidin-1-yl-ethoxy)-phenyl]-5, 6,7,8-tetrahydro-phthalene-2-ol;

cis-1-[6'-pyrrolodinoethoxy-3'-pyridyl]-2-phenyl-6-hydroxy-1,2,3,4-trahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814 (the disclosure of which is hereby incorporated by reference). U.S. Pat. No. 4,133,814 discloses derivatives of 2-phenyl-3-aroyl-benzothiophene and 2-phenyl-3-aroylbenzothiophene-1-oxide.

The following paragraphs provide preferred dosage ranges for various anti-resorptive agents.

The amount of the anti-resorptive agent to be used is determined by its activity as a bone loss inhibiting agent. This activity is determined by means of an individual compound's pharmacokinetics and its minimal maximal effective dose in inhibition of bone loss using a protocol such as those referenced above.

In general an effective dosage for the activities of this invention, for example the treatment of osteoporosis, for the estrogen agonists/antagonists (when used in combination with (L)-(+)-tartaric acid salt of the compound of Formula I of this invention) is in the range of 0.01 to 200 mg/kg/day, preferably 0.5 to 100 mg/kg/day.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day.

In particular, an effective dosage for tamoxifen is in the range of 0.1 to 100 mg/kg/day, preferably 0.1 to 5 mg/kg/day.

In particular, an effective dosage for cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl-5,6,7,8-tetrahydro-naphthalene-2-ol;

cis-1-(6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol; or 1-(4'-pyrrolidinolethoxyphenyl)-2-phenyl-6-hydroxy-1,2,3,4-tetrahydroisoquinoline is in the range of 0.0001 to 100 mg/kg/day, preferably 0.001 to 10 mg/kg/day.

In particular, an effective dosage for 4-hydroxy tamoxifen is in the range of 0.0001 to 100 mg/kg/day, preferably 0.001 to 10 mg/kg/day.

Assay for stimulation of GH release from rat pituicytes

Compounds that have the ability to stimulate GH secretion from cultured rat pituitary cells are identified using the following protocol. This test is also useful for comparison to standards to determine dosage levels. Cells are isolated from pituitaries of 6-week old male Wistar rats. Following decapitation, the anterior pituitary lobes are removed into cold, sterile Hank's balanced salt solution without calcium or magnesium (HBSS). Tissues are finely minced, then subjected to two cycles of mechanically assisted enzymatic dispersion using 10 U/mL bacterial protease ($EC_{3.4.24.4}$, Sigma P-6141, St Louis, Mo.) in HBSS. The tissue-enzyme mixture is stirred in a spinner flask at 30 rpm in a 5% $CO_2$ atmosphere at about 37° C. for about 30 min., with manual trituration after about 15 min. and about 30 min. using a 10-mL pipet. This mixture is centrifuged at 200×g for about 5 min. Horse serum (35% final concentration) is added to the supernatant to neutralize excess protease. The pellet is resuspended in fresh protease (10 U/mL), stirred for about 30 min. more under the previous conditions, and manually triturated, ultimately through a 23-gauge needle. Again, horse serum (35% final concentration) is added, then the cells from both digests are combined, pelleted (200×g for about 15 min.), resuspended in culture medium (Dulbecco's Modified Eagle Medium (D-MEM) supplemented with 4.5 g/L glucose, 10% horse serum, 2.5% fetal bovine serum, 1% non-essential amino acids, 100 U/mL nystatin and 50 mg/mL gentamycin sulfate, Gibco, Grand Island, N.Y.) and counted. Cells are plated at $6.0–6.5\times10^4$ cells per $cm^2$ in 48-well Costar™ (Cambridge, Mass.) dishes and cultured for 3–4 days in culture medium.

Just prior to GH secretion assay, culture wells are rinsed twice with release medium, then equilibrated for about 30 minutes in release medium (D-MEM buffered with 25 mM Hepes, pH 7.4 and containing 0.5% bovine serum albumin at 37° C.). Test compounds are dissolved in DMSO, then diluted into pre-warmed release medium. Assays are run in quadruplicate. The assay is initiated by adding 0.5 mL of release medium (with vehicle or test compound) to each culture well. Incubation is carried out at about 37° C. for about 15 minutes, then terminated by removal of the release medium, which is centrifuged at 2000×g for about 15 minutes to remove cellular material. Rat growth hormone concentrations in the supernatants are determined by a standard radioimmunoassay protocol described below.

Measurement of rat growth hormone

Rat growth hormone concentrations were determined by double antibody radioimmunoassay using a rat growth hormone reference preparation (NIDDK-rGH-RP-2) and rat growth hormone antiserum raised in monkey (NlDDK-anti-rGH-S-5) obtained from Dr. A. Parlow (Harbor-UCLA Medical Center, Torrence, Calif.). Additional rat growth hormone (1.5 U/mg, #G2414, Scripps Labs, San Diego, Calif.) is iodinated to a specific activity of approximately 30 $\mu$Ci/$\mu$g by the chloramine T method for use as tracer. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation. This assay has a working range of 0.08–2.5 $\mu$g rat growth hormone per tube above basal levels.

Assay for Exogenously-Stimulated Growth Hormone Release in the Rat after Intravenous Administration of Test Compounds Twenty-one day old female Sprague-Dawley rats (Charles River Laboratory, Wilmington, Mass.) are allowed to acclimate to local vivarium conditions (24° C., 12 hr light, 12 hr dark cycle) for approximately 1 week before compound testing. All rats are allowed access to water and a pelleted commercial diet (Agway Country Food, Syracuse N.Y.) ad ilbitum. The experiments are conducted in accordance with the NIH Guide for the Care and Use of Laboratory Animals.

On the day of the experiment, test compounds are dissolved in vehicle containing 1% ethanol, 1 mM acetic acid and 0.1% bovine serum albumin in saline. Each test is conducted in three rats. Rats are weighed and anesthetized via intraperitoneal injection of sodium pentobarbital (Nembutol®, 50 mg/kg body weight). Fourteen minutes after anesthetic administration, a blood sample is taken by nicking the tip of the tail and allowing the blood to drip into a microcentrifuge tube (baseline blood sample, approximately 100 µl). Fifteen minutes after anesthetic administration, test compound is delivered by intravenous injection into the tail vein, with a total injection volume of 1 mL/kg body weight. Additional blood samples are taken from the tail at 5, 10 and 15 minutes after compound administration. Blood samples are kept on ice until serum separation by centrifugation (1430×g for 10 minutes at 10° C.). Serum is stored at −80° C. until serum growth hormone determination by radioimmunoassay as described above.

Assessment of Exogenously-Stimulated Growth Hormone Release in the Dog after Oral Administration On the day of dosing, the test compound is weighed out for the appropriate dose and dissolved in water. Doses are delivered at a volume of 0.5–3 mL/kg by gavage to 2–4 dogs for each dosing regimen. Blood samples (5 mL) are collected from the jugular vein by direct vena puncture pre-dose and at 0.17, 0.33, 0.5, 0.75, 1, 2, 4, 6, 8 and 24 hours post dose using 5 mL vacutainers containing lithium heparin. The prepared plasma is stored at −20° C. until analysis.

Measurement of Canine Growth Hormone

Canine growth hormone concentrations are determined by a standard radioimmunoassay protocol using canine growth hormone (antigen for iodination and reference preparation AFP-1983B) and canine growth hormone antiserum raised in monkey (AFP-21452578) obtained from Dr. A. Parlow (Harbor-UCLA Medical Center, Torrence, Calif.). Tracer is produced by chloramine T-iodination of canine growth hormone to a specific activity of 20–40 µCi/µg. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation. This assay has a working range of 0.08–2.5 µg canine GH/tube.

Assessment of Canine Growth Hormone and Insulin-Like Growth Factor-1 Levels in the dog after chronic oral administration The dogs receive test compound daily for either 7 or 14 days. Each day of dosing, the test compound is weighed out for the appropriate dose and dissolved in water. Doses are delivered at a volume of 0.5–3 mL/kg by gavage to 5 dogs for each dosing regimen. Blood samples are collected at days 0, 3, 7, 10 and 14. Blood samples (5 ml) are obtained by direct venipuncture of the jugular vein at pre-dose, 0.17, 0.33, 0.5, 0.754, 1, 2, 3, 6, 8, 12 and 24 hours post administration on days 0, 7 and 14 using 5 ml vacutainers containing lithium heparin. In addition, blood is drawn pre-dose and 8 hours on days 3 and 10. The prepared plasma is stored at −20° C. until analysis.

Female Rat Study

This study evaluates the effect of chronic treatment with a GHRP mimetic on weight, body composition and non-fasting plasma concentrations of glucose, insulin, lactate and lipids in estrogen-deficient and estrogen-replete female rats. Acute responsiveness of serum GH levels to i.v. administration of the GH releasing agent was assessed on the last day of dosing. Body weight was monitored weekly throughout the treatment period; additionally, body composition and plasma levels of glucose, insulin, lactate, cholesterol and triglycerides were assessed at the end of treatment.

Virgin female Sprague-Dawley rats were obtained from Charles River Laboratories (Wilmington, Mass.) and underwent bilateral ovariectomy (Ovx) or sham-surgery (Sham) at approximately 12 weeks of age. For sham surgeries, ovaries were exteriorized and replaced into the abdominal cavity. Following surgery the rats were housed individually in 20 cm×32 cm×20 cm cages under standard vivarium conditions (about 24° C. with about 12 hours light/12 hours dark cycle). All rats were allowed free access to water and a pelleted commercial diet (Agway ProLab 3000, Agway Country Food, Inc., Syracuse, N.Y.). The experiment was conducted in accordance with NIH Guidelines for the Care and Use of Laboratory Animals.

Approximately seven months post-surgery, Sham and Ovx rats were weighed and randomly assigned to groups. Rats were dosed daily by oral gavage with 1 mL of either vehicle (1% ethanol in distilled-deionized water), 0.5 mg/kg or 5 mg/kg of a growth hormone releasing agent for 90 days. Rats were weighed at weekly intervals throughout the study. Twenty-four hours after the last oral dose, the acute response of serum growth hormone (GH) to test agent was assessed by the following procedure. Rats were anesthetized with sodium pentobarbital 50 mg/kg. Anesthetized rats were weighed and a baseline blood sample (~100 µl) was collected from the tail vein. Test agent (growth hormone releasing agent or vehicle) was then administered intravenously via the tail vein in 1 mL. Approximately ten minutes after injection, a second 100 µl blood sample was collected from the tail. Blood was allowed to clot at about 4° C., then centrifuged at 2000×g for about 10 minutes. Serum was stored at about −70° C. Serum growth hormone concentrations were determined by radioimmunoassay as previously described. Following this procedure, each anesthetized rat underwent whole body. scanning by dual-energy X-ray absorptiometry (DEXA, Hologic QDR 1000/W, Waltham Mass.). A final blood sample was collected by cardiac puncture into heparinized tubes. Plasma was separated by centrifugation and stored frozen as described above.

Plasma insulin is determined by radioimmunoassay using a kit from Binax Corp. (Portland, Me.). The interassay coefficient of variation is <10%. Plasma triglycerides, total cholesterol, glucose and lactate levels are measured using Abbott VP™ and VP Super System® Autoanalyzer (Abbott Laboratories, Irving, Tex.), using the A-Gent™ Triglycerides, Cholesterol and Glucose Test reagent systems, and a lactate kit from Sigma, respectively. The plasma insulin, triglycerides, total cholesterol and lactate lowering activity of a growth hormone releasing peptide (GHRP) or GHRP mimetic such as a compound of Formula I, are determined by statistical analysis (unpaired t-test) with the vehicle-treated control group.

The (L)-(+)-tartaric acid salt of the compound of Formula I can be administered by oral, parenteral (e.g., intramuscular, intraperitoneal, intravenous or subcutaneous injection, or implant), nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the (L)-(+)-tartaric acid salt of the compound of Formula I is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of the (L)-(+)-tartaric acid salt of the compound of Formula I in the compositions of this invention may be varied; however, it is necessary that the amount thereof be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals, to obtain effective release of growth hormone.

A preferred dosage range is 0.01 to 5.0 mg/kg of body weight daily which can be administered as a single dose or divided into multiple doses.

The following scheme illustrates the synthesis of the (L)-(+)-tartaric acid salt of the compound of Formula I. The symbol "*" indicates a stereochemical center. In the scheme "Prt" is used to indicate any suitable amine protecting group that will be known to those skilled in the art.

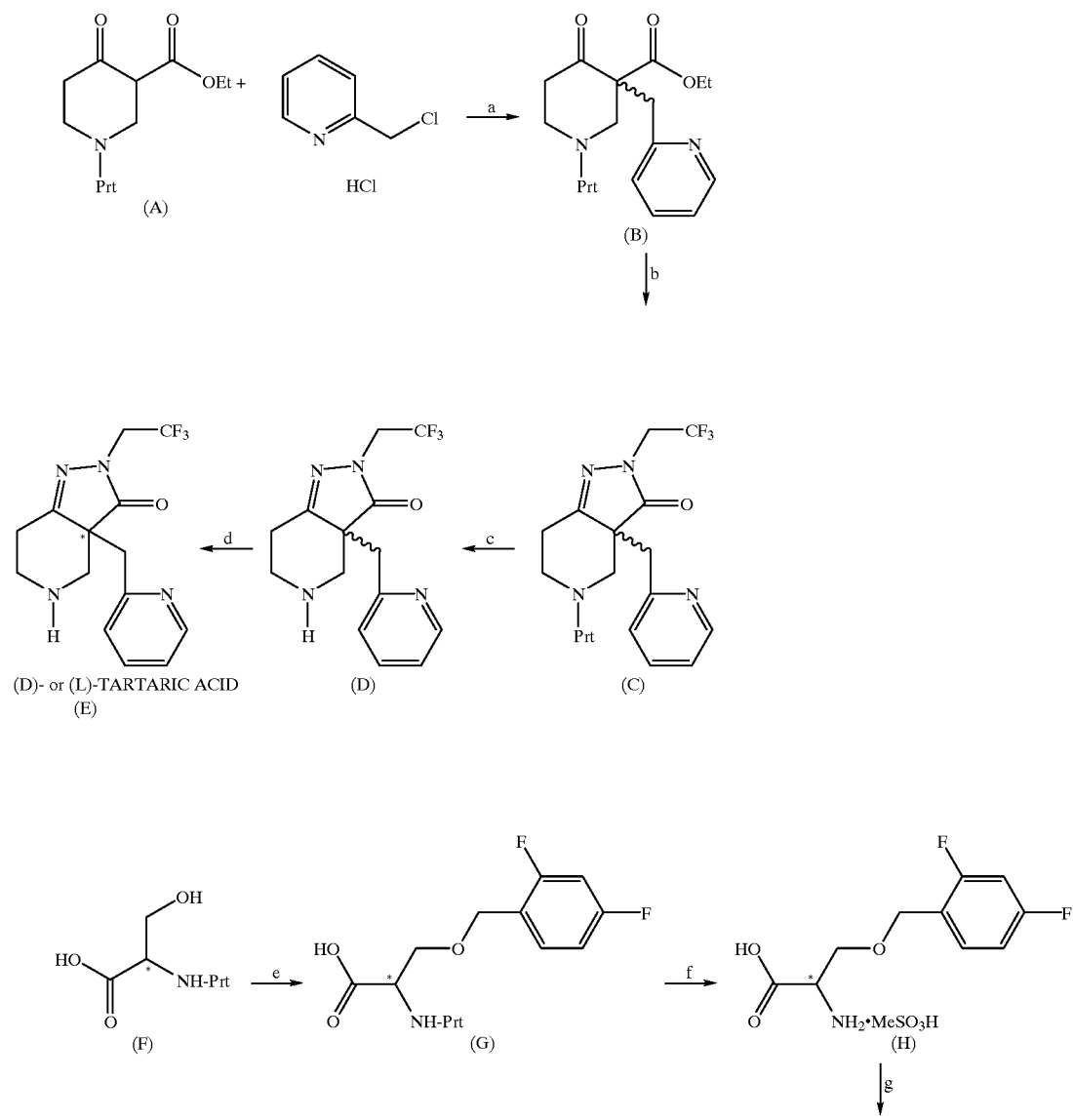

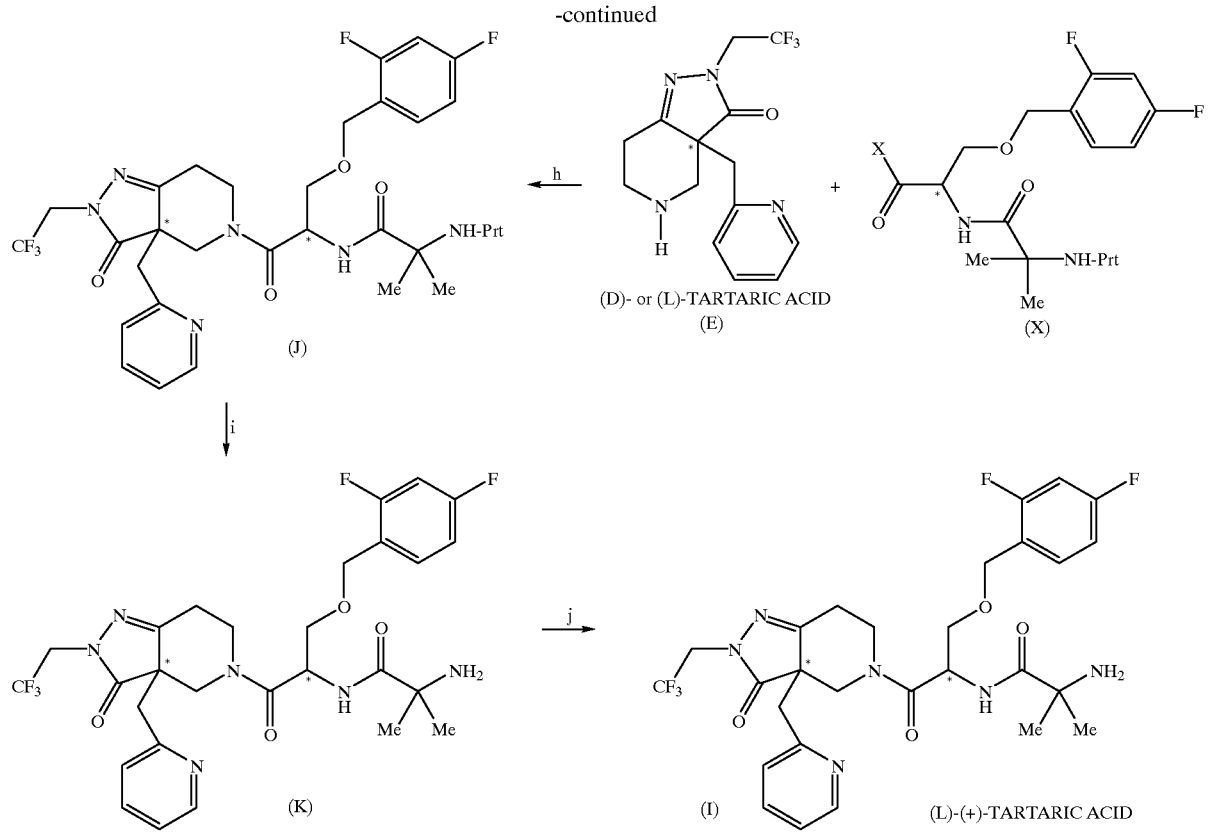

(J), (E), (D)- or (L)-TARTARIC ACID, (X), (K), (I), (L)-(+)-TARTARIC ACID

The following describes the steps of the reactions illustrated in the foregoing scheme. In the following description, the amine protecting group Prt is illustrated with the preferred amine protecting group BOC.

Step a:

To a solution of compound A in a reaction inert polar aprotic solvent such as acetone, methyl ethyl ketone or preferably DMF (dimethylformamide) at about 0° C. to room temperature, preferably 0° C., is added picolyl chloride hydrochloride, a carbonate such as $Li_2CO_3$, $CsCO_3$ or preferably potassium carbonate and potassium iodide or tetrabutylammonium iodide. After stirring at about −20° C. to about 70° C., preferably 0° C. for about 2 to 16 hours, preferably for about 2 hours, the ice bath is removed and DABCO (1,4-diazobicyclo[2.2.2]octane) is added. The reaction mixture is stirred for about 15–30 min. and poured into a mixture of water and a non-polar organic solvent such as toluene, diethyl ether or preferably IPE (isopropyl ether). The organic layer is separated and worked-up using standard methods known in the art to yield compound B.

Step b:

A 70% aqueous solution of $CF_3CH_2NHNH_2$ is used as an aqueous solution in ethanol, water or toluene, preferably the 70% aqueous solution of $CF_3CH_2NHNH_2$ is extracted with toluene. To a solution of compound 8 in an organic solvent such as ethanol or preferably toluene, is first added the toluene extracts containing the anhydrous 2,2,2-trifluoroethyl hydrazine, followed by acetic acid. The reaction mixture is heated at about 60°–110° C., preferably 70° C., for about 30 minutes to 12 hours, preferably 2 hours. The reaction mixture is cooled to room temperature and neutralized with an aqueous base such as $NaHCO_3$. The organic layer is separated and worked-up using standard methods known in the art to yield compound C.

Step c:

An acid such as HCl in IPE or ethanol, triflic acid or an alkyl sulfonic acid such as methanesulfonic acid is added to a solution of compound C in a reaction inert organic solvent such as EtOH, IPE or preferably $CH_2Cl_2$. The mixture is stirred for about 1–2 hours, then cooled to about 0° C. to room temp., preferably 0° C., and then an amine base, such as triethylamine, or $NH_4OH$ is added to the mixture. The mixture is allowed to warm to room temperature, diluted with additional organic solvent and worked-up using standard methods known in the art to yield compound D.

Step d:

(D)- or (L)-Tartaric acid, preferably (D)-tartaric acid, is added to Compound D in acetone/water (about 8:1 to about 9:1) at about room temperature. The mixture is stirred at room temperature for about 15 minutes to overnight, preferably overnight, the solid is filtered, collected and washed with cold acetone, to yield the compound of formula E, preferably compound E is the (D)-tartrate of a single enantiomer.

Step e:

To a solution of N-BOC-serine, preferably N-BOC-(D)-serine, (compound F) in THF/DMF (about 1:1 to about 2:1) at about 0° C. is added n-BuLi or a potassium tert-butoxide solution. The reaction mixture is stirred at about 0° C. for about 10–30 min. preferably 20 min., then 2,4-difluorobenzyl bromide is added. After warming to room temperature and stirring for about 6–24 hours, the reaction mixture is concentrated in vacuo to remove the THF and an aqueous acid such as 1 N HCl is added to adjust the mixture to pH of about 3. The reaction mixture is then partitioned between water and an organic solvent such as $CH_2Cl_2$ or IPE. The organic solution is worked-up using standard methods known in the art to yield compound G, preferably having the R-configuration at the stereocenter, also known as the (D)-enantiomer.

Step f:

To a solution of compound G in an organic solvent such as THF, $CH_2Cl_2$, IPE or a mixture thereof, preferably $CH_2Cl_2$/IPE (about 1:1), is added an alkyl sulfonic acid such as methanesulfonic acid. The solid is filtered and washed with a $CH_2Cl_2$/IPE mixture (1:1) to afford compound H, preferably having the R-configuration at the stereocenter, also known as the (D)-enantiomer.

Step g:

To a solution of compound H in THF/water (about 4:1) is added 2-tert-butoxycarbonylamino-2-methyl-propionic acid-2,5-dioxo-pyrrolidin-1-yl ester and an alkyl amine such as triethylamine. The reaction mixture is stirred at room temperature for about 1–24 hours and quenched with an aqueous acid such as 10% aqueous citric acid solution. The mixture is partitioned with an organic solvent such as ethyl acetate and the organic layer is separated and worked-up using standard methods known in the art to yield compound X, preferably having the R-configuration at the stereocenter also known as the (D)-enantiomer. Compound X can be an acid, alkyl ester or acid halide (X is OH, —$O(C_1-C_4)$alkyl or halo), the acid is preferred.

Step h:

(a) Compound E, preferably the (D)-tartrate of a single enantiomer, is added at about −35° to 0° C., preferably at about −6° C. to ethyl acetate. The solution is cooled to about −30 to −50° C., then an alkyl amine such as triethylamine is added. The reaction mixture is stirred for about 30–90 min. at a temperature between about −78° C. and about −20° C., and filtered to give a solution of the free base of compound E.

(b) When X in compound X is OH, compound X, preferably having the R-configuration at the stereocenter, is added at about −78° C. to −20° C., preferably −35° C. to a reaction inert organic solvent such as ethyl acetate solution containing the free base of compound E from step h(a), an alkyl amine such as triethylamine and PPAA (1-propane phosphonic acid cyclic anhydride) (50% in ethyl acetate). The reaction mixture is stirred for about 1–24 hours, and worked-up using standard methods known in the art to yield compound J, preferably having the absolute and relative 3a-(R), 1-(R) configuration.

When X in compound X is Cl, compound X is added at about −78° C. to a reaction inert solvent such as dichloromethane solution containing the free base of compound E and an alkyl amine such as triethylamine. The reaction mixture is stirred for about 1–24 hours at about 0–30° C. and then worked up using standard methods known in the art to yield compound J, preferably having the absolute and relative 3a-(R), 1-(R) configuration.

When X in compound X is —$O(C_1-C_4)$alkyl, where methyl is preferred, compound X is added to a solution of the free or conjugate base of E (the conjugate base of compound E (—NM where M=Li, Na, K, Mg or Al, preferably aluminum) is prepared by reacting the free amine base with the appropriate reagent (i.e. M=Li, butyl lithium or LDA, M=Na, NaH or $NaN(SiMe_3)_2$ or M=K, KH or $KN(SiMe_3)_2$, or M=Mg, any alkyl Grignard reagent, preferably diethyl magnesium bromide, or M=Al any trialkyl aluminum reagent, preferably trimethyl aluminum)), preferably aluminum, in a reaction inert solvent such as dichloromethane and the resulting reaction mixture is stirred for about 1–24 hours at about −20–110° C. and worked-up using standard methods known in the art to yield compound J, preferably having the absolute and relative 3a-(R), 1-(R) configuration.

Step i:

An acid such as HCl in EtOH, methanesulfonic acid or triflic acid in $CH_2Cl_2$ is added at about 0° C. to room temperature to compound J in $CH_2Cl_2$, IPE or THF. The mixture is stirred for about 40 minutes to about 4 hours at room temperature, then a saturated aqueous base such as $NaHCO_3$ is added until the solution is at neutral pH. The organic layer is separated and worked-up using standard methods known in the art to yield compound K, preferably having the absolute and relative 3a-(R), 1-(R) configuration.

Step j:

To a solution of compound K in an alcohol preferably methanol is added L-(+) tartaric acid. The reaction mixture is stirred for about 1-12 hours, filtered and concentrated. The crude residue is diluted with an organic solvent such as ethyl acetate, heated and slowly allowed to cool to room temperature. The solid is filtered and dried to give the L-(+) tartaric acid salt of the compound of Formula I as white crystals, preferably having the absolute and relative 3a-(R), 1-(R) configuration.

The following example is provided for the purpose of further illustration only and is not intended to be a limitation on the disclosed invention.

Silica gel was used for column chromatography. Melting points were taken on a Buchi 510 apparatus and are uncorrected. Proton NMR spectra were recorded on a Varian XL-300, Bruker AC-300, Varian Unity 400 or Bruker AC-250 at 25° C. Chemical shifts are expressed in parts per million down field from trimethylsilane.

EXAMPLE 1

2-Amino-N-{1-(2,4-difluoro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4,3-c]pyridin-5yl]-ethyl}-2-methyl-propionamide L-(+) tartrate A. 4-Oxo-3-pyridin-2-ylmethyl-piperidine-1,3-dicarboxylic acid 1-tert-butyl ester 3-ethyl ester To a solution of 4-oxo-piperidine-1,3-dicarboxylic acid 1-tert-butyl ester 3-ethyl ester (10.34 g, 38.2 mmol) in DMF (40 mL) at about 0° C. was added picolyl chloride hydrochloride (5.7 g, 34.7 mmol), potassium carbonate (14.4 g, 104.1 mmol) and potassium iodide (5.76 g, 34.7 mmol). After stirring at about 0° C. for about 2 hours, the ice bath was removed and DABCO (973 mg, 8.68 mmol) was added. The reaction mixture was stirred for about 30 min. and poured into a mixture of water and IPE. The organic layer was separated and washed with saturated aqueous $NaHCO_3$ and saturated aqueous NaCl, dried over $Na_2SO_4$ and concentrated in vacuo. The crude residue was crystallized from hexanes to give a white solid (8.19 g, yield 65%). $^1$H-NMR ($CDCl_3$) δ1.17 (t, 3H), 1.48 (s, 9H), 1.55 (s, 2H), 2.61 (m, 1H), 2.71 (m, 1H), 3.31–3.50 (m, 3H), 4.11 (d, 2H), 4.49 (d, 1H), 7.06 (br s, 1H), 7.17(d, 1H), 7.54 (m, 1H), 8.40 (s, 1H).

B. 3-Oxo-3a-pyridin-2-ylmethyl-2-(2,2,2-trifluoro-ethyl)-2,3,3a,4,6,7-hexahydro-pyrazolo[4,3-c]pyridine-5-carboxylic acid tert-butyl ester A 70% aqueous solution of $CF_3CH_2NHNH_2$ (325 mL, 1.986 mol) (obtained from Aldrich) was extracted with toluene (3×1200 mL). To a solution of the product made according to step A (600 g, 1.655 mol) in toluene (900 mL) was first added the combined toluene extracts containing the anhydrous 2,2,2-trifluoroethyl hydrazine, followed by acetic acid (121.4 g, 1.986 mol). The reaction mixture was heated at about 70° C. for about 2 hours then another toluene extractlon of 70% aqueous 2,2,2-trifluoroethyl hydrazine (50 g) was added. The reaction mixture was heated at about 80° C. for about 3.5 hours, cooled to room temperature and diluted with saturated aqueous $NaHCO_3$ (2 L). The toluene layer was separated and washed with saturated aqueous NaCl, dried over $Na_2SO_4$ and concentrated in vacuo to give an oil (754.8 g). Crystallization from methanol/water afforded the desired product as a white solid (609.5 g). $^1$H-NMR (CDCl$_3$) δ 1.50 (s, 9H), 2.53 (d, 1H), 2.70 (br s, 2H), 2.88 (br s, 1H), 3.31 (m, 2H), 3.97 (m, 1H), 4.19 (m, 1H), 4.46 (br s, 1H), 4.63 (br s, 1H), 7.06 (m, 2H), 7.51(m, 1H), 8.34 (m, 1H).

C. 3a-Pyridin-2-ylmethyl-2-(2,2,2-trifluoroethyl)-2,3a,4,5,6,7-hexahydro-pyrazolo[4,3-c]pyridin-3-one Methanesulfonic acid (11.6 g, 121 mmol) was added dropwise to a solution of the product from step B (10 9, 24.2 mmol) in CH$_2$Cl$_2$ (100 mL) over about 30 minutes. The reaction mixture was stirred for about 1 hour, then cooled to about 0° C., and then triethylamine (18.6 mL, 133.1 mmol) was added through an addition funnel. The mixture was allowed to warm to room temperature over about 1 hour, diluted with additional CH$_2$Cl$_2$ and washed with saturated aqueous NaCl, dried over Na$_2$SO$_4$, filtered and concentrated in vacuo to afford the product as a white solid (7.2 g). $^1$H-NMR (CDCl$_3$) δ: 2.51–2.72 (m, 41), 3.35 (m, 2H), 3.49 (m, 2H), 4.03 (m, 1H), 4.25 (m, 1H), 7.08 (d, 2H), 7.51 (t, 1H), 8.37 (d, 1H).

D. 3a-Pyridin-2-ylmethyl-2-(2,2,2-trifluoroethyl)-2,3a,4,5,6,7-hexahydro-pyrazolo[4,3-c]pyridin-3-one (D)-tartrate In a dry and nitrogen purged 5 L round bottom flask equipped with a mechanical stirrer, D-(−) tartaric acid (129 g, 0.86 mol) was added to the compound made according to step C (243 g, 0.78 mol) in acetone/water (9:1, 2430 mL) at about 17° C. The mixture was stirred at room temperature overnight, filtered, the solid was collected and washed with cold acetone and dried under vacuum. The product was obtained as a yellow solid (284 g, yield 78.8%).

E. 2-tert-Butoxycarbonylamino-3-(2,4-difluoro-benzyloxy)-propionic acid

To a solution of N-Boc-(D)-serine (452 9, 2.2026 mol) in a mixture of THF (7 L) and DMF (3 L) at about 0° C. was added potassium tert-butoxide solution (515.8 g, 4.5963 mol). The reaction mixture was stirred at about 0° C. for about 30 min., then 2,4-difluorobenzyl bromide (456.5 g, 2.2051 mol) was added. After warming to room temperature, the reaction mixture was concentrated in vacua to remove the THF. Partitioned the reaction mixture between 4.5 L H$_2$O and 4.5 L IPE. Separated the layers and adjusted the pH of the aqueous layer with 1 N HCl to about 3. The aqueous layer was extracted twice with 4 L each of IPE. The organic solution was dried over Na$_2$SO$_4$, and concentrated in vacuo to yield a yellow waxy solid (518.0 g, yield: 70.9 %). $^1$H-NMR (CDCl$_3$) δ1.44 (s, 9H), 3.73 (m, 1H), 3.94 (d, 1H), 4.44 (br s, 1H), 4.54 (s, 2H), 5.34 (m, 1H), 6.78 (m, 1H), 6.84 (m, 1H), 7.30 (m, 1H).

F. 2-Amino-3-(2,4-difluoro-benzyloxy)-propionic acid, methanesulfonic acid salt

To a solution of the product from step E (1.19 g, 3.59 mmol) in CH$_2$Cl$_2$/IPE (1:1, 12 mL) was added methanesulfonic acid (1.72 g, 17.95 mmol) through a syringe over about 10 minutes. A solid immediately precipitated out of solution. After about 1 hour, the solid was filtered and washed with a CH$_2$Cl$_2$/IPE mixture (1:1) to afford 939 mg of product (yield 80 %).

G. 2-(2-tert-Butoxycarbonylamino-2-methyl-propionylamino)-3-(2,4-difluoro-benzyloxyl-propionic acid To a solution of the product from step F (520 mg, 1.46 mmol) in THF/water (4:1, 10 mL) was added 2-tert-butoxycarbonylamino-2-methyl-propionic acid-2,5-dioxo-pyrrolidin-1-yl ester (438 mg, 1.46 mmol) and triethylamine (369 mg, 3.65 mmol). The reaction mixture was stirred at room temperature for about 1 hour and quenched with a 10% aqueous citric acid solution (10 mL). After about 15 min., ethyl acetate (50 mL) was added and the organic layer was separated and washed with saturated aqueous NaCl, dried over Na$_2$SO$_4$ and concentrated in vacuo to give a foam (534.1 mg, yield 88 %). $^1$H-NMR (CD$_3$OD): δ1.38 (br s, 15H), 3.77 (d, 1H), 3.92 (d, 1H), 4.52 (m, 3H), 6.92 (m, 1H), 7.41 (m, 1H), 7.58 (d, 1H).

H. (1-{1-(2,4-Difluoro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4.3-c]pyridin-5-yl]-methylcarbamoyl}-1-methyl-ethyl)-carbamic acid tert-butyl ester (a) To the compound made according to step D (517 g, 1.12 mol) was added at about −6° C. to ethyl acetate (5170 mL) in a dry and nitrogen purged 12 L round bottom flask equipped with a mechanical stirrer. The solution was cooled to about −40° C., then triethylamine (398 mL, 2.86 mol) was added over about 45 minutes. The reaction mixture was stirred for about 90 min. at a temperature between about −50° C. and about −40° C., filtered into a 22 L round bottom flask purged with nitrogen and washed with ethyl acetate (2068 mL, pre-cooled to about −50° C.) to give the free base as a white solid.

(b) The compound made according to step G (425 g, 1.02 mol) was added at about −30° C. to an ethyl acetate solution containing the product from step H(a), triethylamine (654 mL, 4.69 mol) and PPAA (1-propanephosphonic acid cyclic anhydride) (50% in ethyl acetate, 916 mL, 1.53 mol). The reaction mixture was stirred for about 1 hour, washed with water and saturated aqueous NaCl, dried over Na$_2$SO$_4$ and concentrated in vacuo to give the product as an oil (636 g, yield: 87.8%).

I. 2-Amino-N-{1-(2,4-difluoro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide Methanesulfonic acid (258.3 mL, 3.98 mol) was added dropwise at about 15° C. over about 55 minutes to the product from step H (566 9, 0.796 mol) in CH$_2$Cl$_2$ (11,320 mL) in a dry and nitrogen purged 22 L round bottom flask equipped with a mechanical stirrer. The mixture was stirred for about 40 minutes at about 20° C., then saturated aqueous NaHCO$_3$ (8,490 mL) was added until the pH was about 7.8. The organic layer was separated, washed with water and saturated aqueous NaCl, dried over Na$_2$SO$_4$, and concentrated in vacuo to afford an oily product (388.8 9, yield 80%).

J. 2-Amino-N-{1-(2,4-difluoro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide L-(+) tartrate To a solution of the product from step I (370 9, 0.6 mol) in methanol (4,070 mL) in a 12 L round bottom flask equipped with a mechanical stirrer was added L-(+) tartaric acid (90 g, 0.6 mol). The reaction mixture was stirred for about 90 min. at about 22° C., filtered and concentrated. The crude residue was diluted with ethyl acetate (4,560 mL), heated at about 70° C. and slowly allowed to cool to room temperature over about 17 hours. The solid was filtered and dried to give white crystals, mp 188–189° C. (348.46 g, yield 76%). $^1$H NMR (MeOH, d4) 3: 8.28 (d, 1H), 7.59 (t, 1H), 7.41–7.39 (m, 1H), 7.18–7.13 (m, 1H), 6.92 (t, 1H), 5.2 (t, 1H), 4.56 (bs, 3H), 4.36 (s, 2H), 4.31–4.25 (m, 1H), 4.13–4.06 (m, 1H), 3.78 (d, 2H), 3.21 (t, 1H), 3.18–2.96 (m, 2H), 2.65–2.55 (m, 2H), 1.57 (d, 6H). MS: MH+ 611. $[α]_{589}$ +22.03 (c=1 1.9, MeOH).

What is claimed is:

1. The (L)-(+)-tartaric acid salt of the compound of Formula I

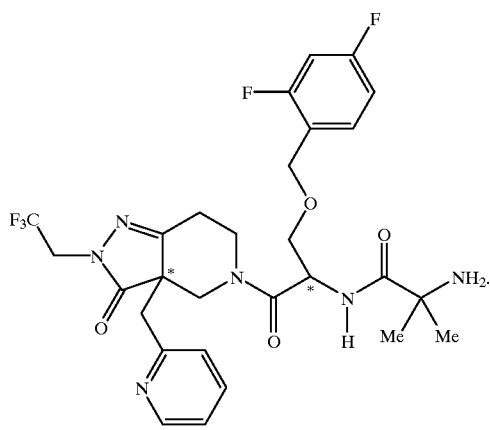

2. The (L)-(+)-tartaric acid salt of the compound of formula I according to claim 1 wherein the stereochemical configuration is 3a-S, 1-R.

3. The (L)-(+)-tartaric acid salt of the compound of formula I according to claim 1 wherein the stereochemical configuration is 3a-S, 1-S.

4. The (L)-(+)-tartaric acid salt of the compound of formula I according to claim 1 wherein the stereochemical configuration is 3a-R, 1-S.

5. The (L)-(+)-tartaric acid salt of the compound of formula I according to claim 1 wherein the stereochemical configuration is 3a-R, 1-R.

6. A process for the preparation of the (L)-(+)-tartaric acid salt of the compound of formula I,

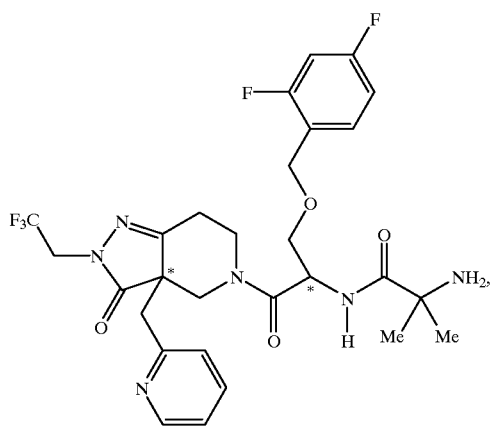

which comprises reacting the compound of formula (E),

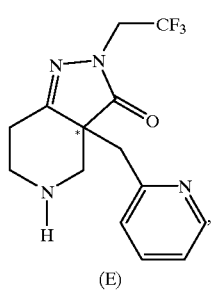

with the compound of formula (X),

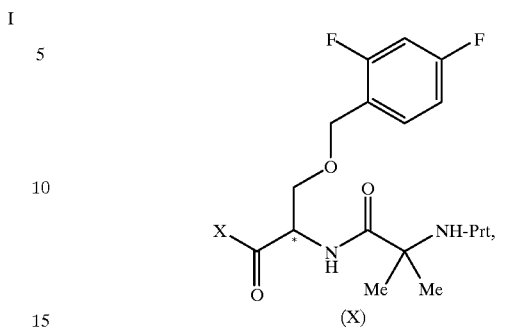

where Prt is an amine protecting group and X is OH, —O($C_1$–$C_4$)alkyl or halo, in the presence of an organic base and a peptide coupling reagent at a temperature between about −78° C. to about −20° C., to yield the compound of formula (J),

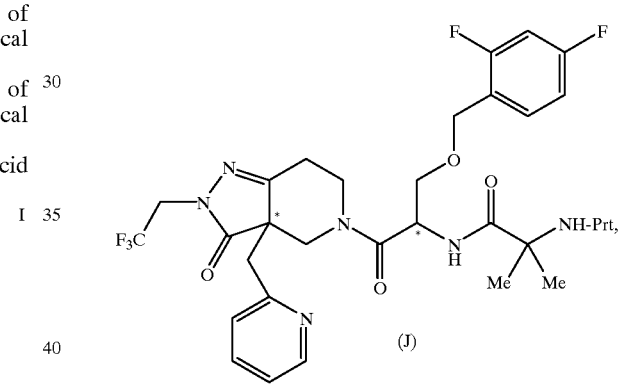

deprotecting the compound of formula (J) under appropriate deprotecting conditions to yield the compound of formula (K),

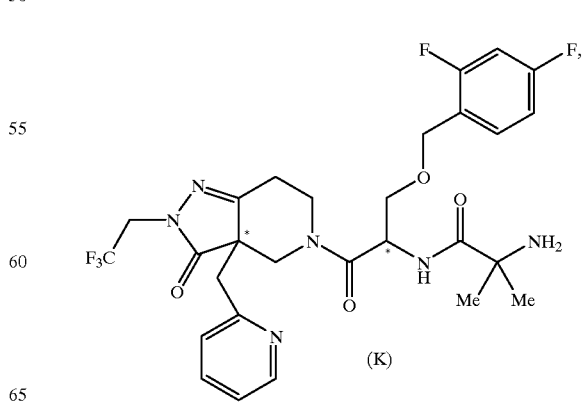

reacting the compound of formula (K) with (L)-(+)-tartaric acid in a reaction inert solvent to yield the (L)-(+)-tartaric acid salt of the compound of formula I.

7. A process according to claim 6 where Prt is tert-butoxycarbonyl.

8. A process according to claim 7 where the peptide coupling reagent is 1-propane phosphonic acid cyclic anhydride and the compound of formula I has the absolute and relative configuration 3a-(R), 1-(R).

9. A method for increasing levels of endogenous growth hormone in a human or an animal which comprises administering to the human or animal an effective amount of the (L)-(+)-tartaric acid salt of the compound of formula I according to claim 1.

10. A pharmaceutical composition which comprises a pharmaceutically-acceptable carrier and an amount of the (L)-(+)-tartaric acid salt of the compound of formula I according to claim 1.

11. A pharmaceutical composition useful for increasing the endogenous production or release of growth hormone in a human or an animal which comprises a pharmaceutically acceptable carrier, an effective amount of the (L)-(+)-tartaric acid salt of the compound of formula I according to claim 1 and a growth hormone secretagogue selected from the group consisting of GHRP-6, Hexarelin, GHRP-1, growth hormone releasing factor (GRF), IGF-1, IGF-2 and B-HT920 or an analog thereof.

12. A method for treating osteoporosis which comprises administering to a human or an animal in need of the treatment an amount of the (L)-(+)-tartaric acid salt of the compound of formula I according to claim 1 which is effective in treating osteoporosis.

13. A method for treating or preventing diseases or conditions which are treated by growth hormone which comprises administering to a human or an animal in need of the treatment an amount of the (L)-(+)-tartaric acid salt of the compound of formula I according to claim 1 which is effective in promoting release of endogenous growth hormone.

14. A method according to claim 13 wherein the disease or condition is congestive heart failure, obesity or frailty associated with aging.

15. A method according to claim 14 wherein the disease or condition is congestive heart failure.

16. A method according to claim 13 wherein the disease or condition is frailty associated with aging.

17. A method for accelerating bone fracture repair, attenuating protein catabolic response after a major operation, reducing cachexia and protein loss due to chronic illness, accelerating wound healing, or accelerating the recovery of burn patients or patients having undergone major surgery, which method comprises administering to a mammal in need of the treatment an amount of the (L)-(+)-tartaric acid salt of the compound of formula I according to claim 1 which is effective in promoting release of endogenous growth hormone in said manual.

18. A method according to claim 17 wherein the method is for accelerating the recovery of patients having undergone major surgery.

19. A method according to claim 17 wherein the method is for accelerating bone fracture repair.

20. A method for improving muscle strength, mobility, maintenance of skin thickness, metabolic homeostasis or renal homeostasis, which method comprises administering to a human or an animal in need of the treatment an amount of the (L)-(+)-tartaric acid salt of the compound of formula I according to claim 1 which is effective in promoting release of endogenous growth hormone.

21. A method for the treatment of osteoporosis which comprises administering to a human or an animal with osteoporosis effective amounts of a bisphosphonate compound and the (L)-(+)-tartaric acid salt of the compound of formula I according to claim 1.

22. A method for the treating osteoporosis according to claim 21 wherein the bisphosphonate compound is ibandronate.

23. A method for the treatment of osteoporosis according to claim 21 wherein the bisphosphonate compound is alendronate.

24. A method for the treatment of osteoporosis which comprises administering to a human or an animal with osteoporosis effective amounts of estrogen or Premarin® and the (L)-(+)-tartaric acid salt of the compound of formula I according to claim 1 and, optionally, progesterone.

25. A method for the treatment of osteoporosis which comprises administering to a human or other animal with osteoporosis effective amounts of calcitonin and the (L)-(+)-tartaric acid salt of the compound of formula I according to claim 1.

26. A method for increasing IGF-1 levels in a human or an animal deficient in IGF-1 which comprises administering to a human or an animal with IGF-1 deficiency an effective amount of the (L)-(+)-tartaric acid salt of the compound of formula I according to claim 1.

27. A method for the treatment of osteoporosis which comprises administering to a human or an animal with osteoporosis effective amounts of an estrogen agonist or antagonist and the (L)-(+)-tartaric acid salt of the compound of formula I according to claim 1.

28. A method according to claim 27 wherein the estrogen agonist or antagonist is tamoxifen, droloxifene, raloxifene or idoxifene.

29. A method according to claim 27 wherein the estrogen agonist or antagonist is cis-6-(4-fluoro-phenyl)-5-[4-(2-piperidin-1-yl-ethoxy)-phenyl]-5,6,7,8-tetrahydro-naphthalen-2-ol; (−)-cis-6-phenyl-5-[4-(2-pyrrolidin-1-yl-ethoxy)-phenyl]-5,6,7,8-tetrahydro-naphthalen-2-ol; cis-6-phenyl-5-[4-(2-pyrrolidin-1-yl-ethoxy)-phenyl]-5,6,7,8-tetrahydro-naphthalen-2-ol; cis-1-[6'-pyrrolodinoethoxy-3'-pyridyl]-2-phenyl-6-hydroxy-1,2,3,4-tetrahydro-naphthalene; 1(4'-pyrrolidinoethoxyphenyl)-2-(4"-fluorophenyl)-6-hydroxy-1,2,3,4-tetrahydroisoquinoline; cis-6-(4-hydroxyphenyl)-5-[-(2-piperidin-1-yl-ethoxy)-phenyl]-5,6,7,8-tetrahydro-naphthalen-2-ol; or 1-(4'-pyrrolidinolethoxyphenyl)-2-phenyl-6-hydroxy-1,2,3,4-tetrahydro-isoquinoline.

30. A method for increasing muscle mass, which method comprises administering to a human or an animal in need of the treatment an effective amount of the (L)-(+)-tartaric acid salt of the compound of formula I according to claim 1.

31. A method for promoting growth in growth hormone deficient children which comprises administering to a growth hormone deficient child an effective amount of the (L)-(+)-tartaric acid salt of the compound of formula I according to claim 1.

32. A method for treating insulin resistance in a mammal, which comprises administering to said mammal an effective amount of the (L)-(+)-tartaric acid salt of the compound of formula I according to claim 1.

33. A method according to claim 32 wherein the condition associated with insulin resistance is type I diabetes, type II diabetes, hyperglycemia, impaired glucose tolerance or an insulin resistant syndrome.

34. A method according to claim 32 wherein the condition associated with insulin resistance is associated with obesity or old age.

35. A method for increasing levels of endogenous growth hormone, which comprises administering to a human or an animal in need thereof effective amounts of a functional somatostatin antagonist and the (L)-(+)-tartaric acid salt of the compound of formula I according to claim 1.

36. A method according to claim 35 wherein the functional somatostatin antagonist is an alpha-2 adrenergic agonist.

37. A method of treating congestive heart failure, obesity or frailty associated with aging, which comprises administering to a human or an animal in need thereof effective amounts of a functional somatostatin antagonist and the (L)-(+)-tartaric acid salt of the compound of formula I according to claim 1.

38. A method of treating sleep disorders in a mammal suffering from sleep disorders comprising administering to said mammal an effective amount of the (L)-(+)-tartaric acid salt of the compound of formula I according to claim 1.

* * * * *